(12) United States Patent
Cigainero

(10) Patent No.: US 10,751,256 B1
(45) Date of Patent: Aug. 25, 2020

(54) PACIFIER AROME SYSTEM AND METHOD USE

(71) Applicant: Stephanie Cigainero, Plano, TX (US)

(72) Inventor: Stephanie Cigainero, Plano, TX (US)

( * ) Notice: Subject to any disclaimer, the term of this patent is extended or adjusted under 35 U.S.C. 154(b) by 63 days.

(21) Appl. No.: 15/366,906

(22) Filed: Dec. 1, 2016

Related U.S. Application Data

(60) Provisional application No. 62/261,724, filed on Dec. 1, 2015.

(51) Int. Cl.
  *A61J 17/00* (2006.01)
  *A61M 25/00* (2006.01)
  *A61J 7/00* (2006.01)
  *A61M 15/00* (2006.01)

(52) U.S. Cl.
  CPC ........ *A61J 7/0053* (2013.01); *A61M 15/0026* (2014.02)

(58) Field of Classification Search
  CPC ........ A61J 17/006; A61J 17/00; A61J 17/001; A61J 17/008; A61J 17/002; A61J 17/003; A61J 17/004; A61J 17/005; A61J 17/007; A61M 15/0026
  See application file for complete search history.

(56) References Cited

U.S. PATENT DOCUMENTS

| | | | | |
|---|---|---|---|---|
| 5,512,047 | A * | 4/1996 | Dvorak | A61J 17/006 604/77 |
| 6,547,808 | B2 * | 4/2003 | Tuckey | A61J 7/0046 604/77 |
| 6,557,548 | B1 * | 5/2003 | Dickson | A61M 15/00 128/200.24 |
| D630,334 | S * | 1/2011 | Paige | D24/194 |
| 2004/0040556 | A1 * | 3/2004 | Fillyaw | A61M 16/0488 128/202.16 |
| 2007/0021783 | A1 * | 1/2007 | Viana | A61M 15/08 606/234 |

FOREIGN PATENT DOCUMENTS

WO  WO-2012020157 A1 *  2/2012  ............ A61J 17/006

* cited by examiner

*Primary Examiner* — Tuan V Nguyen
(74) *Attorney, Agent, or Firm* — Eldredge Law Firm

(57) ABSTRACT

A system includes a pacifier, an aroma device secured to the pacifier, and an aroma scented material. The pacifier includes a solid body with a front surface and a back surface; and a nipple secured to and extending from the front surface. The aroma device includes a housing secured to and protruding from the back surface of the body, the housing forming an inner cavity. The an aroma scented material is removably secured within the inner cavity.

3 Claims, 4 Drawing Sheets

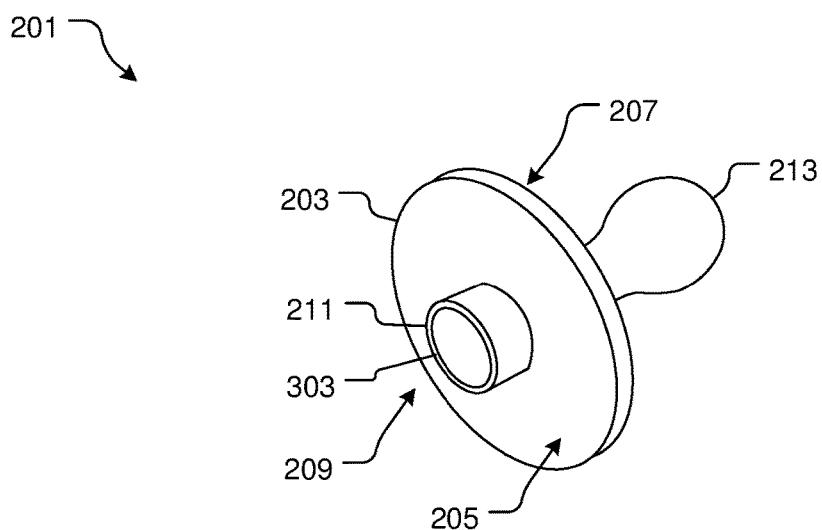
FIG. 2
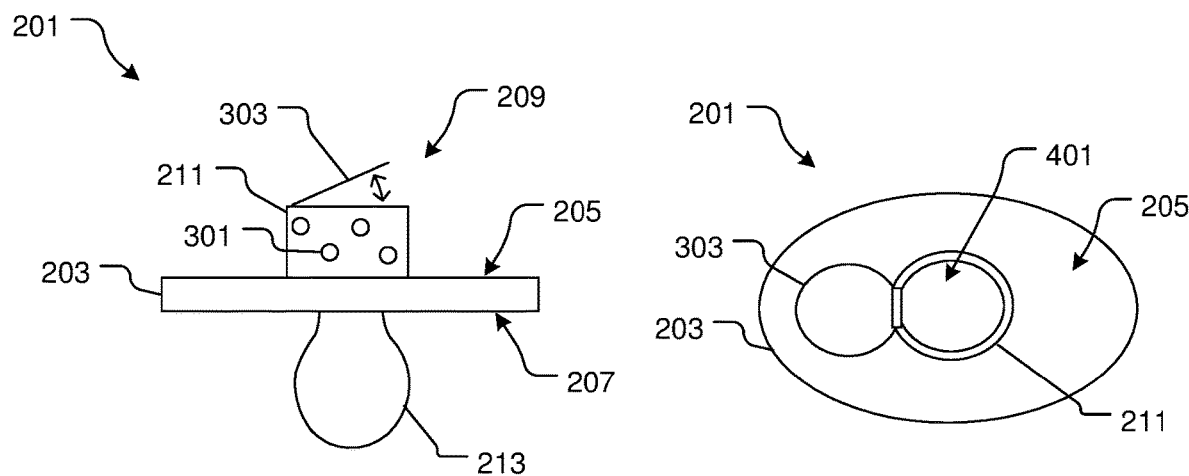
FIG. 3
FIG. 4

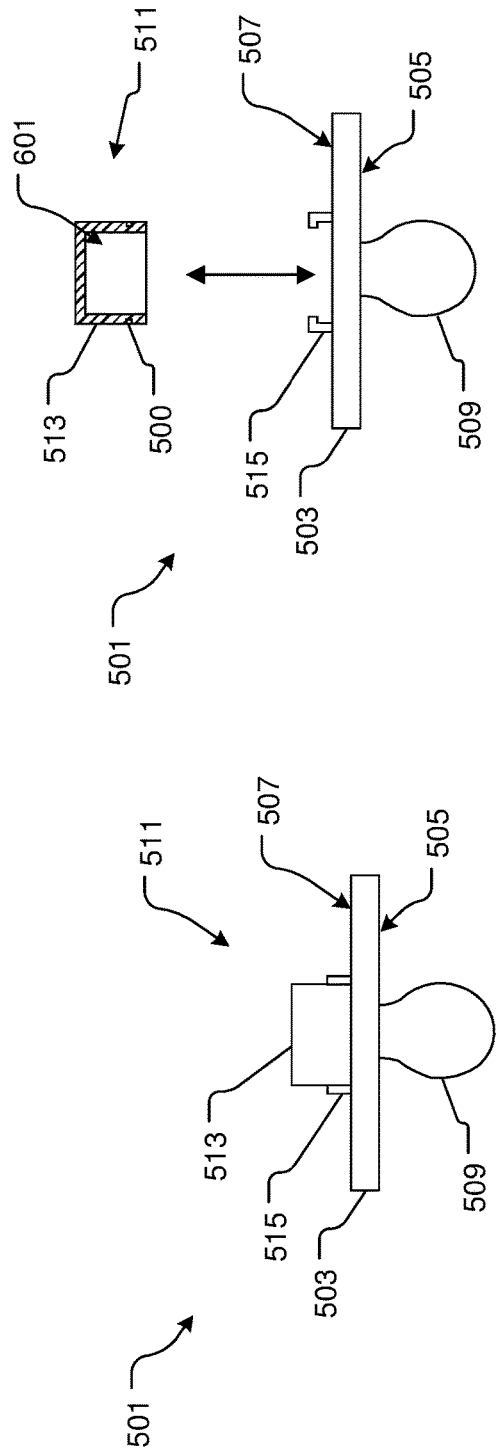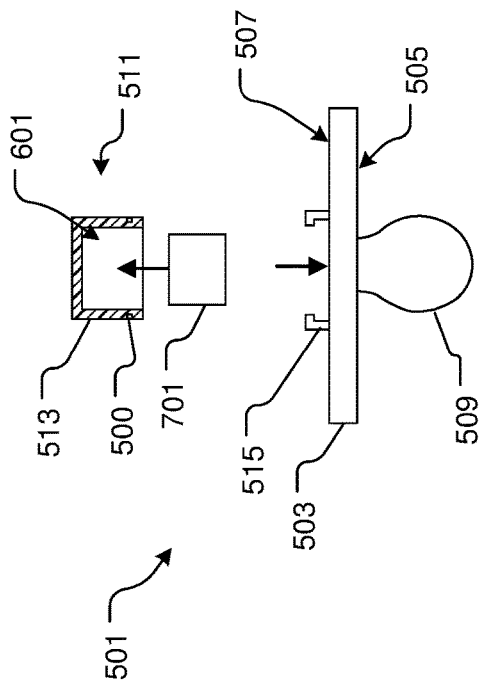

PACIFIER AROME SYSTEM AND METHOD USE

BACKGROUND

1. Field of the Invention

The present invention relates generally to aroma devices, and more specifically, to a pacifier having an aroma device.

2. Description of Related Art

Infant pacifiers are well known in the art and are effective means for soothing effects. In FIG. 1, an oblique view of a conventional pacifier 101 is depicted having a base 103 with opposing surfaces 105, 107. A nipple 113 extends from surface 107, while a fastening means 109 having a ring 111 is attached to surface 105. During use, the infant (not shown) sucks on nipple 113, which in turn creates a soothing effect.

Although great strides have been made in the area of pacifiers, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 2 is an oblique view of a system and method of use in accordance with a preferred embodiment of the present application;

FIG. 3 is a side view of the system of FIG. 2 during use;

FIG. 4 is a top view of the system of FIG. 2 during use;

FIG. 5 is a side view of a system in accordance with an alternative embodiment;

FIG. 6 is a partial cross-sectional view of the system of FIG. 5;

FIG. 7 is a side view of a system in accordance with an alternative embodiment.

Figure 1:
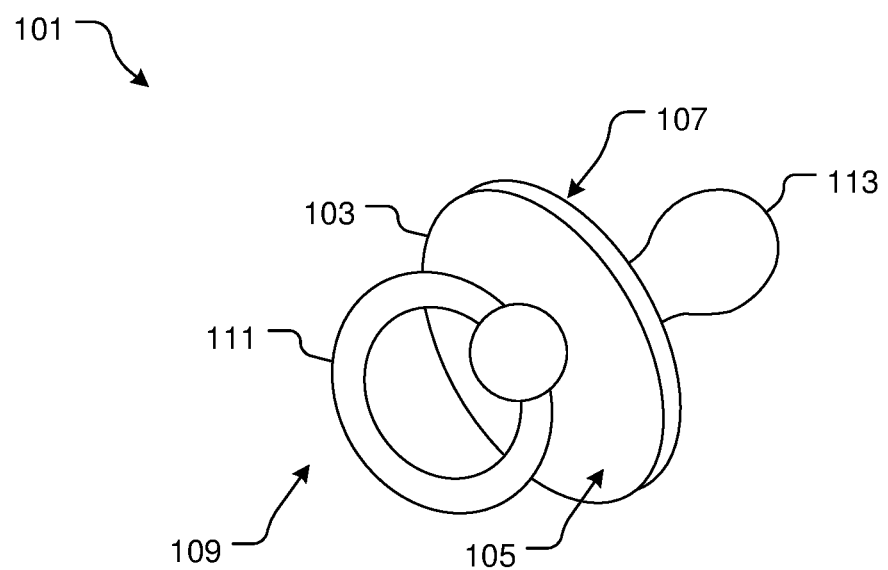
FIG. 1 is an oblique view of a common pacifier.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 2 depicts an oblique view of a pacifier 201 with an aroma device 209 in accordance with a preferred embodiment of the present application. It will be appreciated that pacifier 201 overcomes one of more of the above-listed problems commonly associated with the conventional pacifiers.

One of the unique features believed characteristic of the present invention is the ability to utilize a combination of a pacifier and an aroma device such that the infant (not shown) smells substances from the aroma device during sucking action of the pacifier. In addition, the system and method of use is unique in that the method of securing the smelling substance is achieved through one or more fastening means and/or a housing secured to the base. The smelling substance could be, for example, lavender, eucalyptus, milk/honey, and other desired substances. In one application of use, the smelling substance could include medicine and the like.

Referring back to FIG. 2, pacifier 201 includes a body 203 with opposing surfaces 205, 207. A sucking nipple 213 is rigidly attached to and extends from surface 207, while the aroma device 209 is secured to surface 205. In this exemplary embodiment, the aroma device includes a housing 211 rigidly secured to and extending from surface 205. Access to the inner cavity 401 of housing 211 is achieved via a pivotally latched door 303. Accordingly, the housing 211 has a body that forms a cavity 401 that is accessible via door 303.

Referring to FIGS. 3 and 4, the functionality of door 303 is depicted. It will be appreciated that the door 303 is latched to the body of housing 211 via a locking means (not shown). These features allow the user to place the smelling substance within the cavity a secure it therein by latching door 303 to the body of housing 211. In the contemplated embodiment, the body of housing 211 includes a plurality of openings 301 selectively sized to allow a determined amount of scent to pass through the thickness of the body. Accordingly, the openings 301 enable the infant to smell the substance disposed within the cavity during use. In the contemplated embodiment, the openings are fixed in position; however, it is contemplated having adjustable openings, wherein a twisting action of the housing adjusts the exposure of the openings, which in turn adjusts the amount of scent exposed to the infant. In one embodiment, when the housing is pulled and twisted relative to the body of the pacifier, the housing will lock into position exposing a narrow chamber wherein a fragrance moistened wafer can be inserted and the mechanism twisted back into its original position. Twisting the mechanism counterclockwise will adjust the strength of aroma by uncovering various sized holes in progression until twisting is no longer possible and Aroma is fully flowing.

In an alternative embodiment, it is contemplated having a housing removably attached to the base of the pacifier. These features are illustrated in FIGS. 5-7, which depicts a pacifier 501 with an aroma device 511. It will be appreciated that pacifier 501 and aroma device 511 is substantially similar in form and function to pacifier 201 and aroma device 209 discussed above and incorporates one or more of the features discussed herein.

Pacifier 501 includes a base 503 having surfaces 505, 507 with a nipple rigidly attached to and extending from surface 505. The aroma device 511 is removably attached to surface 507. This features is achieved by providing a housing 513 removably attached to a locking device 515 rigidly attached to surface 507 and configured to removably engage with a slot 500 extending inwardly from an outer surface of housing 513. During use, the locking device 515 is manipulated for securing the housing 513 in a fixed position, while also allowing the housing to be separated, as depicted in FIG. 6. It will be appreciated that the locking device could be a pair of clips or a threaded structure wherein the housing can threadedly attach to the pacifier body.

Housing 513 includes a body that forms an inner cavity 601 configured to hold the smelling substances therein. Unlike, the preferred embodiment discussed above, the housing 513 does not include a door for access to cavity 601. Access is achieved by removing the housing from the base via the locking device. As shown in FIG. 7, it is also contemplated having an optional sponge material 701 shaped to fit snugly within cavity 601 and configured to absorb the smelling material in liquid form.

Figure 8:
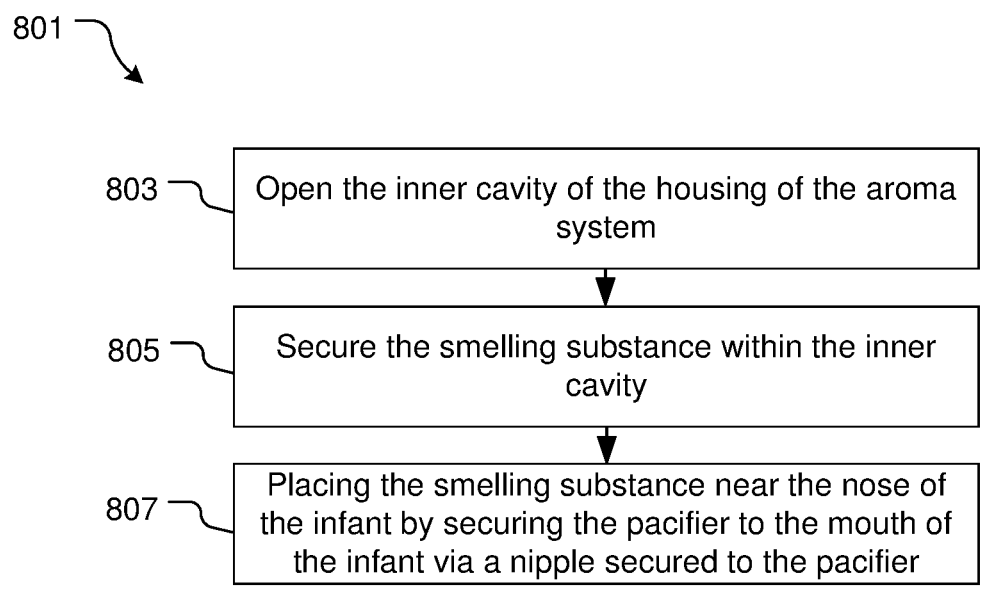
FIG. 8 is a flowchart depicting the preferred process.

Referring now to FIG. 8, a flowchart 801 illustrates the intended use of the different embodiments discussed above. First, the user opens the housing to access the inner cavity, as depicted in box 803. Next, the user places the smelling substance within the inner cavity, as depicted in box 805. It should be noted that the smelling substance could be in liquid form, a sponge, a scented wafer, and the like could be used. The inner cavity is then secured and the aroma from the smelling substance is placed near the nose of the infant by securing the pacifier to the mouth of the infant via a nipple, as depicted in box 807.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system, comprising:
   a pacifier having:
      a solid body with a front surface and a back surface;
      a locking device consisting of a first lip and a second lip protruding from the back surface, each of the one or more lips consisting of a first portion and a second portion, the first portion and second portion being perpendicular;
      a nipple secured to and extending from the front surface;
      an aroma device having:
         a cylindrical housing having a flat top surface and a constant diameter throughout, the cylindrical housing having a first slot and a second slot extending partially into the cylindrical housing from an outer wall and to receive the second portion of the first lip and the second lip and secured to the locking device and protruding from the back surface of the body once engaged with the locking device, the cylindrical housing forming an inner cavity and the outer wall having a plurality of openings extending through a thickness of the outer wall and into the inner cavity, thereby allowing aroma to pass therethrough; and
         an aroma scented material removably secured within the inner cavity such that the aroma scented material is wholly contained between the back surface and the inner cavity, the aroma scented material is a sponge configured to absorb a liquid aroma;
   wherein the housing is configured to engage with the locking device via pressure applied to the housing.

2. A method, comprising: providing the system of claim 1; removably securing the aroma scented material within the inner cavity of the housing; and exuding an aroma scent via the aroma scented material.

3. The method of claim 2, further comprising: exuding the aroma scent through a plurality of holes extending through a thickness of the outer wall and in gaseous communication with the aroma scented material.

* * * * *